United States Patent [19]
Marinescu-Pasoi et al.

[11] Patent Number: 5,158,759
[45] Date of Patent: Oct. 27, 1992

[54] REVERSIBLE STORAGE FOR MEDIA AS WELL AS USE OF THE STORAGE

[75] Inventors: Lucian Marinescu-Pasoi, Frankfurt am Main; Ulrich Behrens, Bad Vilbel; Gunter Langer, Rosbach, all of Fed. Rep. of Germany

[73] Assignee: Battelle-Institut e.V., Frankfurt am Main, Fed. Rep. of Germany

[21] Appl. No.: 546,655

[22] Filed: Jul. 3, 1990

Related U.S. Application Data

[63] Continuation-in-part of Ser. No. 486,215, Feb. 28, 1990, abandoned.

[30] Foreign Application Priority Data

Apr. 3, 1989 [DE] Fed. Rep. of Germany .... P3907084

[51] Int. Cl.$^5$ .................... C01B 3/04; F17C 11/00
[52] U.S. Cl. .................... 423/658.2; 123/3; 126/261; 128/399; 206/0.7; 428/623
[58] Field of Search .............. 206/0.7; 428/623; 423/658.2; 123/3

[56] References Cited

U.S. PATENT DOCUMENTS

| | | | |
|---|---|---|---|
| 3,993,577 | 11/1976 | Black et al. | 252/188 |
| 4,489,049 | 12/1984 | Forester et al. | 423/658.2 |
| 4,839,239 | 6/1989 | Ducos et al. | 428/623 |

FOREIGN PATENT DOCUMENTS

| | | | |
|---|---|---|---|
| 130757 | 1/1985 | European Pat. Off. | |
| 2800903 | 7/1979 | Fed. Rep. of Germany | |
| 32729 | 3/1980 | Japan | 206/0.7 |
| 2051342 | 1/1981 | United Kingdom | |

OTHER PUBLICATIONS

Waide, C. H., et al., "The Application of Metal Hydrides to Ground Transport", in Hydrogen Energy, Part B, Veziroglu, T. N., ed., pp. 779-790, Plenum Press, N.Y. 1975.

Buchner, V. H., "Entwicklungstendenzen von wasserstoffgetriebenen Fahrzeugen mit Hydridspeichern", Haus der Technik, pp. 40–46, 1981.

Neumüller, Dr. O., Römpps Chemie-Lexikon, vol. 4: M-PK, p. 2557.

"Development Trends of Hydrogen-Driven Vehicles with Hydride Storage", Haus der Technick—lecture prepublication, pp. 40–46 (in German, with English translation of highlighted sections).

"Double Range for Hydrogen-Driven Cars", Battelle Information, pp. 6–7, Dec., 1989.

"New Design For Hydrogen Storage System", Vijay et al., Journal of the Less-Common Metals, vol. 106, pp. 263–267 (1985).

Primary Examiner—Wayne Langel
Attorney, Agent, or Firm—Fisher, Christen & Sabol

[57] ABSTRACT

A reversible storage of media, which includes a storage core, an intermediate storage, a catalyst and a protective sheathing. With the opening of the protective sheathing, the stored medium is heated in the catalyst layer, which is caused by the resulting oxygen admission. The storage gets by without any outside heat source, since the binding energy in the intermediate storage is much smaller than that of the main storage, so that the intermediate storage acts as a starter for the reaction. The storage is especially used for heating food including beverages, for heat treating patients in shock and as a quick responding hydrogen storage for release of hydrogen without the input of outside energy.

8 Claims, 2 Drawing Sheets

REVERSIBLE STORAGE FOR MEDIA AS WELL AS USE OF THE STORAGE

This application is a continuation-in-part of our prior applications, U.S. Ser. No. 486,215 filed Feb. 28, 1990, now abandoned.

BACKGROUND OF THE INVENTION

1. Field Of The Invention

The invention relates to reversible storage means for media, with a storage core which with heating releases the stored medium or on which the medium is stored with release of heat.

2. Prior Art

Hydrogen is a particularly "clean" fuel (combustion product: water; no carbon dioxide) and could therefore be widely used in future. To be able to use it to drive vehicles, however, the storage problem must be solved first. This is where metal hydrides for instance come in, which represent a very safe storage medium for hydrogen. What is known as low-temperature hydrides (LTH) so far have been used for this purpose almost exclusively. LTH have the drawback, however, that only a relatively small amount of hydrogen can be stored per kilogram of metal.

High-temperature hydrides (HTH) have about three times the storage capacity of LTH, but require relatively large amounts of heat at high temperatures to release the hydrogen. The exhaust heat from combustion-engine-driven vehicles is insufficient for this, and vehicles with electric (fuel cell) drive produce practically no exhaust heat at all. Consequently, the experiments with HTH have not been very promising so far.

Several embodiments of such reversible storages are known, and reference is made particularly to metal hydrides. But a drawback of the known storages is that they require outside energy for starting. But outside energy is not always available.

For example, "Development Trends of Hydrogen-Driven Vehicles with Hydride Storage", *Haus der technik*, lecture prepublication, pp. 40–46, describes a rechargeable hydride storage arrangement in which a high-temperature hydride storage is coupled to a low-temperature hydride storage. This reference notes, however, (page 41, left column, middle) that "to withdraw hydrogen from the hydride, heat must always be supplied."

The necessity for supplying an outside energy source is disadvantageous, however. For example, in the case where hydrogen is used to drive a motor vehicle, the outside energy is usually sought from the exhaust gas heat. But this energy source is not available when the vehicle is being started. Therefore, another energy source is required to start the engine.

The device is a combination of an HTH storage cell, an LTH storage cell and a catalyst. It is started by inflowing air which triggers catalytic combustion of part of the hydrogen (e.g., from the low-temperature hydride storage); the combustion heat is sufficient to discharge the HTH cell, so that no external heat is needed. Another advantage is that flameless catalytic combustion involves only little pollutant emission and is therefore considerably "cleaner" than additional heating with a flame-producing burner. Catalytic combustion takes place at temperatures below 500° C., which means that nitrogen oxides ($NO_x$) are avoided. If appropriate catalysts are used, hydrogen may even react at 0° C. Catalytic combustion is highly efficient (up to 99.9% fuel utilization). Thermodynamic efficiency is particularly great in all applications requiring low- or medium-temperature heat. Heat losses can be minimized by relatively simple measures.

The device can also be designed as a heat supply unit; in this case the stored hydrogen is used up completely to generate heat. Also, the device makes it possible to fully utilize the excellent safety properties of this storage medium.

BROAD DESCRIPTION OF THE INVENTION

The object of the invention is to provide a reversible storage for media which releases the stored medium without outside energy input. This object of the invention is achieved by the reversible storage and process of the invention.

Other objects and advantages of the invention are set out herein or are obvious herefrom to one skilled in the art.

The invention involves a reversible storage for media which releases the stored medium without outside energy input. The storage core rests on at least one intermediate storage. The latter each rests on a catalyst. The catalyst(s) in turn rests on an airtight protective sheathing, which protects the catalyst or catalysts from the admission of air. If the protective sheathing is removed from the area of the catalyst, atmospheric oxygen enters and causes in the catalyst layer a combustion of the medium, for example, hydrogen, which is released there from the intermediate storage to the catalyst. This heating, thus, starts the process so that the medium stored in the storage core, caused by the development of heat, also releases the medium, preferably also hydrogen, until the storage is emptied. The storage can then be recharged. The process rests, inter alia, on the fact that the binding energy of the medium (e.g., hydrogen) in the intermediate layer is much smaller than in the storage core, so that even at room temperature medium, acting as starter, can go from the intermediate layer into the catalyst layer and there, with air input, release sufficient heat to start and maintain the process also in the main storage.

Preferred materials for the storage core and intermediate storage are metal hydrides.

The storage according to the invention also works with differently designed storage cores and intermediate storages.

A preferred use of the storage according to the invention involves heating food (meals and beverages). It is known for this purpose to feed burnt lime and water into the intermediate space of a double-walled can so that when the can is opened, by the reaction that then takes place heat is generated which heats the food. But in such case corrosive and toxic materials result, i.e., slaked lime, which combined with the danger that these materials may penetrate into the food to be heated, at least after a prolonged storage time of the can, are serious disadvantages. Also reuse is practically ruled out and a further drawback is the greater weight of this known device than the invention device.

A further use of the storage according to the invention is in the heat treatment of patients, especially for shock patients at the site of an accident, where an appropriately-heated cover is not easily available. In this case, the invention storage is designed as a sheet cover.

Another important use of the invention is in the design of this storage as a quickly responding hydrogen storage for the release of hydrogen without the input of outside energy.

If for the storage of hydrogen a metal hydride storage is provided, which is surrounded by a metal catalyst, the catalytic combustion of hydrogen is used for heat development. Such metal catalysts are known in the art.

DETAILED DESCRIPTION OF THE INVENTION

Figure 1:
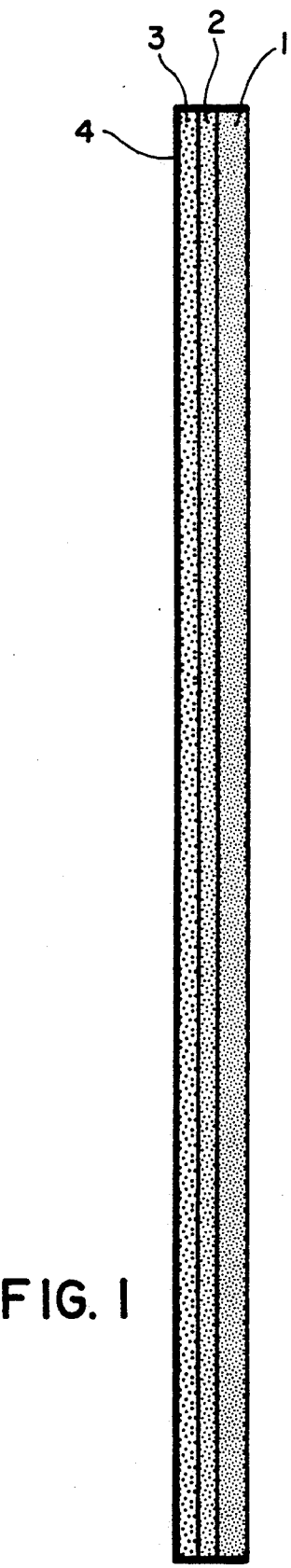
FIG. 1 shows diagrammatically the basic structure of a storage according to the invention.

The invention is explained below in greater detail regarding an embodiment (of the invention), from which other important features of the invention can be seen.

Such embodiment includes (seen from right to left in the figure) storage core 1, which rests on intermediate storage 2. The latter in turn rests on catalyst 3, whose outside is isolated by protective sheathing 4. Protective sheathing 4 surrounds at least the outside of catalyst 3, so that it is guaranteed that no air (oxygen) has access to catalyst 3. Protective sheathing 4 toward the side of intermediate storage 2 or preferably the storage core 1, protects catalyst 3 generally sufficiently from air input.

The mode of operation of the described storage is as follows. Storages 1, 2 are charged with hydrogen and isolated from oxygen input. After opening of protective sheathing 4 the hydrogen, stored in intermediate storage 2, comes out through outside catalytic layer 3. The hydrogen reacts on the surface of catalytic layer 3 with the oxygen present in the air. With this chemical reaction, energy in the form of heat is released. A part of this heat heats the device, and other oxygen from inner hydride storage 1 comes out and also reacts on the surface of catalytic layer 3 with the oxygen present in the air. The heat thus released is then used for heating another medium.

Figure 2:
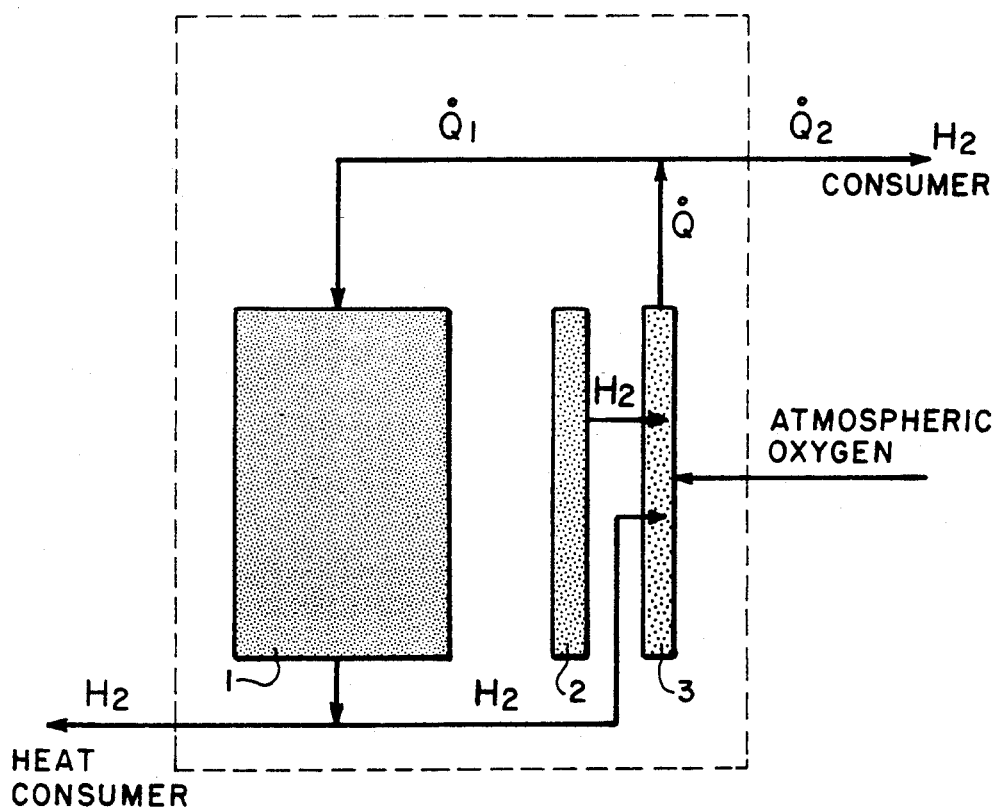
FIG. 2 shows a functional diagram of the basic structure of a storage according to the invention.

The device is described functionally in FIG. 2, wherein $\overline{Q}$, $\overline{Q}_1$, and $\overline{Q}_2$ are the different heat flows, and $H_2$ is the hydrogen. The arrows show that the hydrogen is led optionally to a consumer unit and/or the catalyst (3). $H_2$ also flows from the low-temperature intermediate storage cell—starter cell—(2) to the catalyst (3). The heat flow $\overline{Q}$ moves from the catalyst (3) to the high-temperature main hydride storage cell (1), and may also be supplied to a heat consumer.

Hydrogen may also be supplied from the main HTH storage cell (1) to the low-temperature starter cell (2) in order to recharge the latter. This can be done after the high-temperature storage cell has been heated to a point where it releases the $H_2$. Alternatively, the low-temperature starter cell may also be designed so as to be large enough for containing sufficient hydrogen for several starts or, in extreme cases, for a single start. In any case, the exact design of the device will depend on the particular requirements of the situation at hand.

It would also be possible, of course, to activate the release of hydrogen from the device by feeding to the device outside energy (as is done with prior art devices) if so desired.

The invention device can be reused. Because of the relatively high costs for the materials of the device, the reusability of the device is advantageous.

There are several fields of use for this device:

(A) Heating of beverages and food with a self-heating device. In this case, three representative embodiments are:

1. Self-heating container (can) with a double wall, which contains the medium to be heated, and whose inside walls are designed according to the above invention principle. After opening of the container, air penetrates between the two walls and heat is released.

2. Body (ball, cylinder, etc.), which is designed according to the above invention principle and which after removal of the protective sheathing is immersed in the medium to be heated.

3. Cooker, on which the medium to be heated is heated in a container. The cooker has an airtight container, which contains bodies (balls, cylinders, etc.), which are designed according to the above invention principle. Development of heat is regulated by purposeful air input.

There already exists a self-heating can, but it uses another principle. The heat needed is produced by chemical reaction between burnt lime and water when air is let in. Thus, slaked lime is produced:

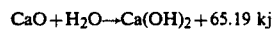

$$CaO + H_2O \rightarrow Ca(OH)_2 + 65.19 \text{ kj}$$

The disadvantages of such prior art device, in contrast with the invention device, are:

higher weight, use and production of caustic and toxic materials (potential danger by penetration into the food), difficult reuse.

(B) Use as quickly responding hydrogen storage without the input of outside energy:

The hydrogen storage has a container, in which the metal hydride and catalyst are located, which are designed according to the above principle. By a controlled air input a part of the stored hydrogen is reacted and causes a heating of the storage and with it the release of the necessary hydrogen. The development of heat takes place at the place in which the stored hydrogen is also located. Thus, an immediate and fast release by hydrogen is guaranteed. No outside heat source is necessary for release of the hydrogen.

Because of the invention device and process, high-temperature hydride storages can be used in the heat recycling of waste gases in a motor vehicle operated with hydrogen. These storages have a higher hydrogen capacity. Until now, the use of high-temperature hydride storages without additional outside heat input was not possible, since heat recycling from combustion processes in the engine was not sufficient for releasing the hydrogen.

(C) As sheet cover in trauma medicine for the heat treatment of shock patients at the site of an accident:

The body temperature of accident victims, e.g., who are in shock, must not drop. Sheets can be designed according to the above invention principle, which are applied to a heat-insulating support and which additionally represent a heat source plus providing heat insulation. The sheets, folded together, are packed in an airtight container, which is opened at the site of the accident.

The advantages of the storage according to the invention reside particularly in the fact that a heating of media can take place in an energy favorable low temperature range (e.g., less than 100° C.). The device does not need any outside energy input. The heat output takes place in a self-regulating way with the suitable selection of design features.

The outside catalytic layer further has the advantage that it prevents an oxidation of the metal hydride storage. As a result, the invention device can be operated even in the presence of oxygen.

The invention device is suitable for an isolated operation and mobile use purposes. It is easy to operate and, in comparison with hydrogen pressure storages or liquid hydrogen storages, represents no potential source of danger for the environment. Further, it is nonpolluting, since in this case a reusable device is involved and in the combustion of the hydrogen only $H_2O$ is generated as waste gas because of the low reaction temperature.

An arrangement of different layers, as is embodied in this device, can also be used for separation of water into hydrogen and oxygen. In this case, the chemical process described above runs in the opposite direction and the resulting oxygen is bound in the storage.

The core of the invention is thus one for the storage of media, which release energy in a chemical reaction and which in addition are in contact with one or more media storages, which can also be used as intermediate storages and in contact with a layer which serves as catalyst for the chemical reaction of the stored medium and which uses a part of the reaction heat directly for heating the storage or storages and thus causes a release of the medium stored in this storage. The entire device is isolated, by suitable measures (protective sheathing, airtight container, etc.), from uncontrolled input of the reactant or reactants of the stored medium.

The design of the device can be shell-shaped, e.g., as a ball, cylinder, etc., or flat, e.g., as a sheet, etc.

What is claimed is:

1. A rechargeable hydride storage arrangement with a high-temperature hydride storage (1) and a low-temperature hydride storage (intermediate storage 2), characterized in that a catalyst (3) is provided, which, with the admission of oxygen, catalytically burns the hydrogen ($H_2$) released from low-temperature hydride storage (2) also without feeding of outside energy, and the thermal energy thus produced heats high-temperature hydride storage (1) so that hydrogen ($H_2$) leaves high-temperature hydride storage (1);

wherein an arrangement (4) is provided for controlling the feeding of atmospheric oxygen to catalyst (3).

2. Hydride storage arrangement according to claim 1, wherein catalyst (3) and high-temperature hydride storage (2) rest against one another by large surfaces; and wherein an arrangement (4) is provided for controlling the feeding of atmospheric oxygen to catalyst (3).

3. Hydride storage arrangement according to claim 2, wherein said arrangement is a protective covering (4).

4. A rechargeable hydride storage arrangement comprising:

a high-temperature hydride storage (1) and a low-temperature hydride storage (intermediate storage 2);

wherein the binding energy of hydrogen ($H_2$) in said low-temperature hydride storage (2) is considerably smaller than in the high-temperature hydride storage (1);

a metal catalyst (3) for catalytically burning hydrogen ($H_2$) and;

openable airtight means (4) for providing a sheathing for said catalyst (3) for isolating at least said metal catalyst (3) from uncontrolled input with oxygen;

wherein, upon opening said airtight means (4), the oxygen admitted thereby caused hydrogen ($H_2$) released from said low-temperature hydride storage (2) to be catalytically burned by the inclusion therewith of said metal catalyst (3) without feeding thereto outside energy; and whereby the thermal energy produced by said catalytic burning of said low-temperature hydride storage (2) heats said high-temperature hydride storage (1) so that hydrogen ($H_2$) leaves said high-temperature hydride storage (1).

5. The rechargeable hydride storage arrangement of claim 4 wherein, prior to opening, said airtight protective sheathing means (4) also covers said low-temperature hydride storage (2) from uncontrolled input of oxygen.

6. The rechargeable hydride storage arrangement of claim 4 wherein, prior to opening, said airtight protective sheathing means (4) also covers said low-temperature hydride storage (2) and said high-temperature hydride storage (1) from uncontrolled input of oxygen.

7. The reversible storage according to claim 4 wherein storage core (1) and intermediate storage (2) are metal hydrides.

8. A process comprising using a hydride storage arrangement with a high-temperature hydride storage (1) and a low-temperature hydride storage (intermediate storage 2), characterized in that a catalyst (3) is provided, which, with the admission of oxygen, catalytically burns the hydrogen ($H_2$) released from low-temperature hydride storage (2) also without feeding of outside energy, and the thermal energy thus produced heats high-temperature hydride storage (1) so that hydrogen ($H_2$) leaves high-temperature storage (1) and drives a motor vehicle operated with hydrogen.

* * * * *